US010426920B2

(12) United States Patent
Sutermeister et al.

(10) Patent No.: US 10,426,920 B2
(45) Date of Patent: Oct. 1, 2019

(54) INTEGRATED CATHETER SYSTEM

(71) Applicant: BOSTON SCIENTIFIC SCIMED, INC., Maple Grove, MN (US)

(72) Inventors: Derek C. Sutermeister, Ham Lake, MN (US); James M. Anderson, Corcoran, MN (US); Timothy A. Ostroot, Cokato, MN (US); Cass A. Hanson, St. Paul, MN (US); Anthony F. Tassoni, Jr., Ramsey, MN (US); Timothy L. Rubesch, Blaine, MN (US); Jan Weber, Maastricht (NL)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 952 days.

(21) Appl. No.: 14/575,675

(22) Filed: Dec. 18, 2014

(65) Prior Publication Data

US 2015/0174363 A1    Jun. 25, 2015

Related U.S. Application Data

(60) Provisional application No. 61/919,565, filed on Dec. 20, 2013.

(51) Int. Cl.
*A61M 25/00* (2006.01)
*A61M 25/01* (2006.01)

(52) U.S. Cl.
CPC ...... *A61M 25/005* (2013.01); *A61M 25/0012* (2013.01); *A61M 25/0053* (2013.01); *A61M 25/0054* (2013.01); *A61M 25/0147* (2013.01); *A61M 2025/015* (2013.01)

(58) Field of Classification Search
CPC ............ A61M 25/0012; A61M 25/005; A61M 25/0147; A61M 2025/0059; A61M 25/0053
USPC ....................................... 604/95.01
See application file for complete search history.

(56) References Cited

U.S. PATENT DOCUMENTS

| 5,002,041 A | * | 3/1991 | Chikama ............. A61B 1/0055 600/139 |
| 6,143,013 A | * | 11/2000 | Samson .............. A61M 25/005 604/264 |
| 6,648,874 B2 | | 11/2003 | Parisi et al. |
| 6,669,886 B1 | | 12/2003 | Willard |
| 6,929,626 B2 | | 8/2005 | DiCarlo et al. |
| 7,413,543 B2 | | 8/2008 | Banik et al. |

(Continued)

FOREIGN PATENT DOCUMENTS

| CN | 102247223 A | 11/2011 |
| EP | 2397108 A2 | 12/2011 |
| WO | 9807523 A1 | 2/1998 |
| WO | 2008031103 A2 | 3/2008 |

*Primary Examiner* — Phillip A Gray
(74) *Attorney, Agent, or Firm* — Seager, Tufte & Wickhem, LLP

(57) ABSTRACT

A guide catheter may include a tubular member having an inner layer defining a lumen extending therethrough, a reinforcing braid disposed about the inner layer, a plurality of steering wires interwoven through the reinforcing braid, and an outer layer disposed about the reinforcing braid. At least a portion of the reinforcing braid may be embedded within the outer layer. An introducer sleeve may be slidably disposed over the tubular member. A flush port element may be operably connected to the introducer sleeve.

20 Claims, 6 Drawing Sheets

(56) References Cited

U.S. PATENT DOCUMENTS

| | | |
|---|---|---|
| 7,569,046 B2 | 8/2009 | Zhou |
| 7,578,786 B2 | 8/2009 | Boulais et al. |
| 7,591,783 B2 | 9/2009 | Boulais et al. |
| 7,922,650 B2 | 4/2011 | McWeeney et al. |
| 8,118,732 B2 | 2/2012 | Banik et al. |
| 8,425,408 B2 | 4/2013 | Boulais et al. |
| 8,475,366 B2 | 7/2013 | Boulais et al. |
| 8,535,219 B2 | 9/2013 | Smith et al. |
| 8,608,648 B2 | 12/2013 | Banik et al. |
| 8,608,649 B2 | 12/2013 | McWeeney et al. |
| 8,636,270 B2 | 1/2014 | Ostrovsky |
| 8,715,270 B2 | 5/2014 | Weitzner et al. |
| 2004/0089969 A1 | 5/2004 | Willard |
| 2004/0143159 A1 | 7/2004 | Wendlandt |
| 2005/0080449 A1* | 4/2005 | Mulder ............. A61F 2/01 606/200 |
| 2005/0119527 A1 | 6/2005 | Banik et al. |
| 2005/0131279 A1 | 6/2005 | Boulais et al. |
| 2005/0245789 A1 | 11/2005 | Smith et al. |
| 2010/0217184 A1 | 8/2010 | Koblish et al. |
| 2012/0004502 A1 | 1/2012 | Weitzner et al. |
| 2012/0123327 A1 | 5/2012 | Miller |
| 2012/0209073 A1 | 8/2012 | McWeeney et al. |
| 2012/0277671 A1* | 11/2012 | Fuentes ............. A61M 25/005 604/95.04 |
| 2013/0172879 A1 | 7/2013 | Sutermeister et al. |
| 2013/0261396 A1 | 10/2013 | Boulais et al. |
| 2013/0289352 A1 | 10/2013 | Boulais et al. |
| 2014/0066706 A1 | 3/2014 | McWeeney et al. |
| 2014/0073852 A1 | 3/2014 | Banik et al. |

* cited by examiner

INTEGRATED CATHETER SYSTEM

CROSS-REFERENCE TO RELATED APPLICATIONS

This application claims priority under 35 U.S.C. § 119(e) to U.S. Provisional Application No. 61/919,565, filed Dec. 20, 2013, the entire disclosure of which is herein incorporated by reference.

FIELD

The disclosure is broadly directed toward devices and methods for accessing a patient's vascular system during medical catheterization procedures. In particular, the disclosure relates to an integrated guide catheter for introducing medical devices and/or therapeutic agents into a body of a patient.

BACKGROUND

Guide catheters may be used in medical catheterization procedures to provide a passageway through which diagnostic and therapeutic medical devices and/or agents may be introduced into a patient's body. In intravascular and coronary applications, some such medical devices may include balloon dilation catheters, guide wires, or other therapeutic devices.

For treatment of certain diseases or conditions, a guide catheter may be inserted into the femoral artery via an introducer sheath and advanced to a target location. An introducer sheath is a device that may be used to access and exchange guide wires and catheters into a bodily lumen. A therapeutic device may be deployed at the target location to perform a desired medical procedure. Once the procedure is completed, the guide catheter and the introducer sheath are removed from the patient.

Catheter placement may have associated risks such as internal bleeding or patient discomfort. Radial and/or brachial approaches have been developed which may reduce these risks. However, there may be certain challenges associated with the radial approach of catheterization. The radial artery is thinner than the femoral artery, and the previously available guide catheters and introducer sheaths may have a larger profile that may not be suitable for insertion into the radial artery. Additionally, guide catheters with a smaller profile may have a smaller inner diameter that may not be sufficient for introduction of the therapeutic device(s).

In some cases, a physician may need to steer the guide catheter through a tortuous path to reach a target location. Additionally, a steerable guide catheter may reduce the number of times an operator needs to exchange the guide catheter, thereby reducing overall procedural time and cost. Some available guide catheters may include steering wires disposed along the outer or the inner surfaces of the guide catheter. Such designs may increase the wall thickness of the guide catheter, thereby increasing its profile and/or reducing the inner lumen diameter. Guide catheters with a larger profile may require a large entry point hole that might not be suitable for the radial approach.

Hence, there is a need for a steerable guide catheter with a small profile.

SUMMARY

A catheter may include an inner layer defining a lumen extending therethrough, a reinforcing braid disposed about the inner layer, a plurality of steering wires interwoven through the reinforcing braid, and an outer layer disposed about the reinforcing braid, wherein at least a portion of the reinforcing braid is embedded within the outer layer.

A catheter system may include a guide catheter including an inner layer defining a lumen extending therethrough, a reinforcing braid disposed about the inner layer, a plurality of steering wires interwoven through the reinforcing braid, an outer layer at least partially disposed about the reinforcing braid, and an introducer sleeve slidably disposed about and supported by the guide catheter. The catheter system may include a flush port element operably connected to the introducer sleeve.

The above summary of some embodiments is not intended to describe each disclosed embodiment or every implementation of the present disclosure. The figures and detailed description which follow more particularly exemplify these embodiments, but are also intended as exemplary and not limiting.

Figure 1:
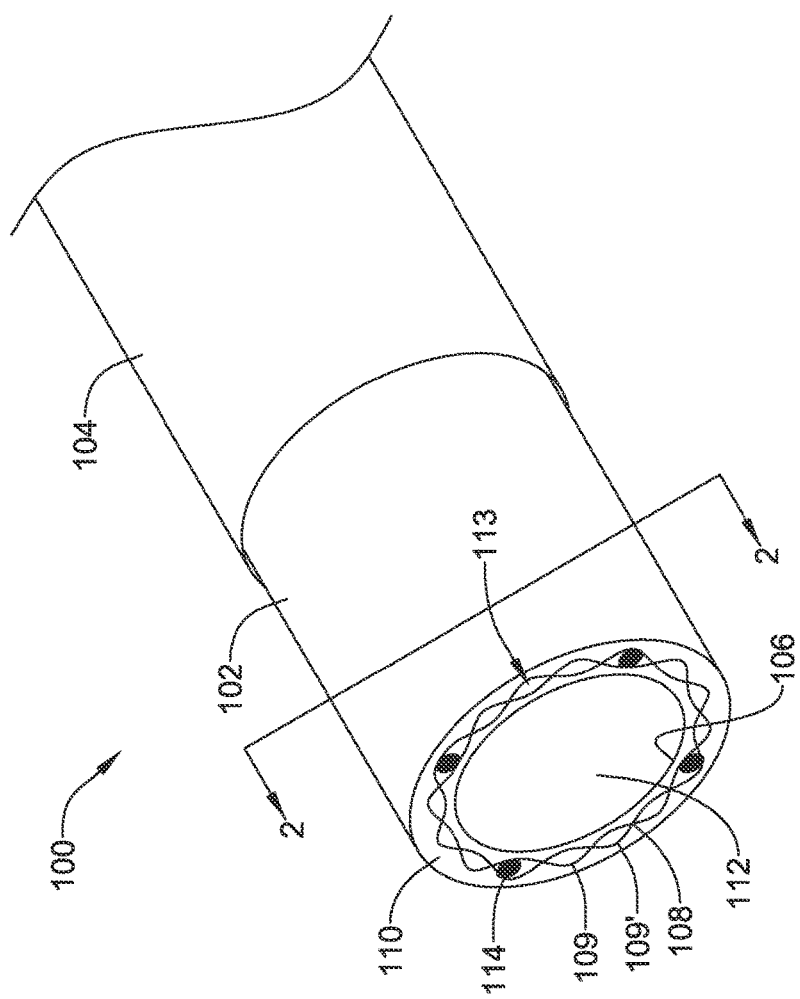
FIG. 1 illustrates a perspective view of a portion of an example guide catheter.

While embodiments of the present disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the present disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

The disclosure may relate to devices and methods for diagnosis and treatment of diseases associated with the blood vessels, for example coronary diseases. In some embodiments, the disclosed guide catheters and guide catheter systems may be used for angiography and angioplasty procedures, but for a person skilled in the art, it is understood that the catheter systems may be used for other medical procedures.

More particularly, the present disclosure may relate to an integrated catheter system having a smaller profile, where the system may include a guide catheter and an introducer sleeve. The catheter system may be used for approaches that require a smaller profile system such as radial approach, brachial approach, or the like. The catheter system may be designed such that it has better torque control capabilities, a smaller profile with a potentially larger inner diameter, and/or improved steering mechanisms.

To achieve the features mentioned above, the catheter system may include a tubular member (i.e., a catheter shaft) and an introducer sleeve disposed about the tubular member. In some embodiments, the introducer sleeve may have a thin wall that may be supported by the catheter shaft, thereby reducing the overall profile of the catheter system. Additionally, the catheter system may include a steering mechanism that may aid in guiding the catheter to a target location. The catheter may include a reinforcing braid that may provide column strength, crush and/or radial collapse resistance, and/or other suitable properties to the catheter to be navigated through a circuitous and/or tortuous path. A steerable, flexible guide catheter may eliminate the need for guide catheter exchange(s). A smaller profile of the catheter may also be achieved by passing the steering wires through the reinforcing braid as it may reduce the thickness of the catheter wall.

The catheter shaft and the introducer sleeve may be introduced together into an artery at an entry point hole or opening. The introducer sleeve may be kept disposed at the entry point hole or opening to protect the entry point hole or opening and the catheter shaft may be advanced to reach the target location.

FIG. 1 is an illustration of a guide catheter 100. The guide catheter 100 may include a tubular member 102 and an introducer sleeve 104 disposed about at least a distal portion of the tubular member 102. The tubular member 102 may include an inner layer 106, a reinforcing braid 108, and an outer layer 110. The inner layer 106 may define a lumen 112 extending along a length of the tubular member 102. The lumen 112 may form the working channel of the guide catheter 100 through which one or more devices may be passed. An inner diameter of the lumen 112 may be sized to allow advancement of a therapeutic device therethrough. In some embodiments, the inner layer 106 may be formed using a suitable material capable of reducing the friction between the inner layer 106 and any therapeutic devices that may be inserted through the lumen 112.

In some embodiments, the reinforcing braid 108 may be disposed about the inner layer 106. The reinforcing braid 108 may include a first plurality of wires 109 and a second plurality of wires 109' interwoven with the first plurality of wires 109. The first plurality of wires 109 and the second plurality of wires 109' may be woven, knitted, entwined, interlocked, or braided together. In some embodiments, the reinforcing braid 108 may form a web-like structure.

In some embodiments, a plurality of steering wires 114 may be passed through and/or interwoven with the reinforcing braid 108. In some embodiments, the plurality of steering wires 114 may include two, three, four, five, six, or other suitable quantity of steering wires. For the purpose of illustration, in FIG. 1, four steering wires 114 may be passed through the reinforcing braid 108. This is just one example and other configurations are contemplated. In some embodiments, the plurality of steering wires 114 may pass through a plurality of interstices 113, or gaps between adjacent wires of the reinforcing braid 108. In some embodiments, the plurality of interstices 113 may be formed or defined by a pattern of the interwoven first plurality of wires 109 and second plurality of wires 109'. In some embodiments, the reinforcing braid 108 may enhance torque control, column strength, crush and/or radial collapse resistance, and/or anti-kink ability of the guide catheter 100 for proper positioning of the guide catheter 100 within the patient's vasculature.

In some embodiments, the tubular member 102 may also include an outer layer 110 disposed about the reinforcing braid 108 such that at least a portion of the reinforcing braid 108 may be embedded within the outer layer 110. The outer layer 110 may give a uniform outer surface to the guide catheter 100 for easy insertion of the guide catheter 100 and minimal damage to surrounding tissue. The outer layer 110 may be formed using a suitable biocompatible material that may provide sufficient smoothness to the outer layer 110.

In some embodiments, the outer layer 110 may include a coating, for example, a coating of a radiopaque material that may allow operator to visualize the guide catheter 100 under fluoroscopy or X-ray imaging. In some embodiments, the coating may also be a coating for increasing the lubricity of the guide catheter as it traverses through the patient's body to the target location.

In some embodiments, an introducer sleeve 104 may be disposed over the outer layer 110 to limit and/or prevent damage to an entry location while the guide catheter 100 is advanced through the entry location toward the target location. The introducer sleeve 104 may be a thin-walled tubular structure that may be supported by the tubular member 102. In some embodiments, the introducer sleeve 104 may have sufficient wall thickness and/or radial strength to avoid collapsing during aspiration (under suction, or greater external pressure than internal pressure) or changing out of the tubular member 102. In some embodiments, the introducer sleeve 104 may rely upon or may depend upon support provided by the tubular member 102 disposed therein to maintain a maximum outer diameter, size, or extent. In some embodiments, the introducer sleeve 104 may collapse radially inward when the tubular member 102 is removed from the lumen of the introducer sleeve. In some embodiments, the introducer sleeve 104 may be made up of same material as that of the inner layer 106 or the outer layer 110.

Figure 2:
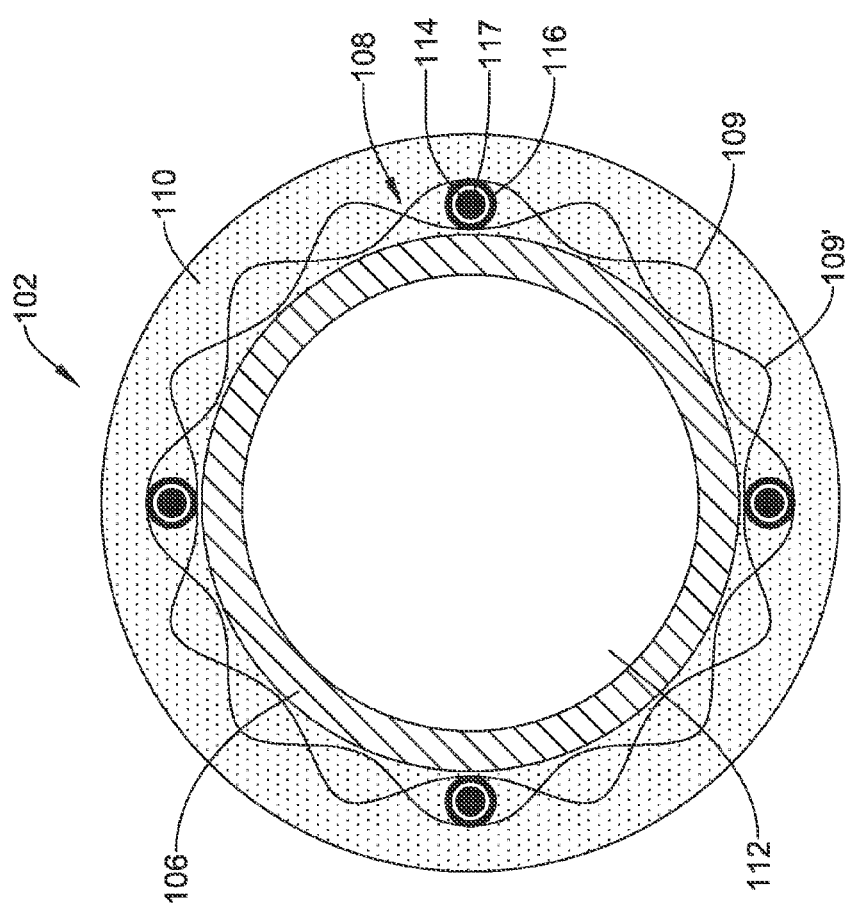
FIG. 2 illustrates a cross-sectional view of the example guide catheter of FIG. 1.

FIG. 2 is a cross-sectional view of the tubular member 102 of the guide catheter 100 as shown in FIG. 1 across a plane 2-2. In some embodiments, the tubular member 102 may include an inner layer 106, a reinforcing braid 108, and an outer layer 110. In some embodiments, the tubular member 102 may have a circular cross-sectional shape. However, other cross-sectional shapes such as, but not limited to, elliptical, oblong, rectangular, or the like are also contemplated.

In some embodiments, the inner layer 106 may be a thin, flexible, tube-like structure that may define a lumen 112 extending through the tubular member 102 along a length of the inner layer 106. In some embodiments, the lumen 112 may be defined to receive therapeutic medical devices or agents.

As shown herein, in some embodiments, the reinforcing braid 108 may be disposed about the inner layer 106. In some embodiments, the reinforcing braid 108 may surround the inner layer 106 and may include a first plurality of wires 109 and a second plurality of wires 109' braided or interwoven together.

The guide catheter 100 may further include a plurality of steering wire sheaths 116. The plurality of steering wire sheaths 116 may each be a tubular structure having a sheath lumen 117 extending therethrough configured to slidably receive one of the plurality of steering wires 114. The plurality of steering wires 114 may each be elongate wires slidably disposed within one sheath lumen 117. The plurality of steering wire sheaths 116 may extend from a proximal end of the tubular member 102 to a distal end of the tubular member 102. Similarly, the plurality of steering wires 114 disposed within the plurality of steering wire sheaths 116 may also extend from the proximal end of the tubular member 102 to the distal end of the tubular member 102.

In some embodiments, a proximal end of some, each, or all of the plurality of steering wires 114 may be connected to a handle disposed at the proximal end of the tubular member 102. In some embodiments, a distal end of some, each, or all of the plurality of steering wires 114 may be fixedly attached to the distal end of the tubular member 102. In some embodiments, the plurality of steering wires 114 may act as a steering mechanism that may deflect the distal end of the guide catheter 100 and/or the tubular member 102 upon actuation. In some embodiments, the plurality of steering wires 114 may be actuated using the handle at the proximal end of the guide catheter 100 and/or the tubular member 102. In some embodiments, the handle may include an electric current control mechanism and a source of electrical energy. In some embodiments, the source of electrical energy may be a battery disposed within the handle or a wire or wires operatively connected to an external source of electrical energy. In some embodiments, the plurality of steering wires 114 may be formed from a material that reacts or responds to electrical energy applied thereto to shorten or lengthen, thereby selectively altering a length of one or more of the plurality of steering wires 114 to deflect the distal end of the guide catheter 100 and/or the tubular member 102. In some embodiments, the plurality of steering wires 114 may be formed from a shape memory alloy such as Flexinol® wires, available from Dynalloy, Inc. in Tustin, Calif., USA. Deflection of the distal tip (distal end) of the guide catheter 100 and/or the tubular member 102 may help the operator to steer the guide catheter 100 and/or the tubular member 102 to the target location through the tortuous anatomy.

In some embodiments, the plurality of steering wires 114 may extend proximal of the proximal end of the tubular member 102 and/or the plurality of steering wire sheaths 116 to a handle, as discussed above, or the proximal end of some, each, or all of the plurality of steering wires 114 may be manually manipulated without the aid of a handle. In some embodiments, the distal end of some, each, or all of the plurality of steering wires 114 may extend distal of the distal end of the tubular member 102 and/or the plurality of steering wire sheaths 116. In some embodiments, the proximal end and/or the distal end of the plurality of steering wires 114 may include a stop or other feature configured to prevent the plurality of steering wires 114 from being pulled through the sheath lumen 117 of the plurality of steering wire sheaths 116.

In some embodiments, the plurality of steering wires 114 may be maintained under tension, such that relieving tension or providing slack in one of the plurality of steering wires 114 may effect steering of the distal end of the guide catheter 100 and/or the tubular member 102 away from the one of the plurality of steering wires 114 that had tension relieved or was slacked. In some embodiments, the plurality of steering wires 114 may be formed of a stretchy or elastic material. In some embodiments, the plurality of steering wires 114 may be rigid, with the other catheter materials and/or additional, separate elements storing and/or providing tension to the plurality of steering wires 114. In some embodiments, springs, such as coil springs for example, may be attached to the plurality of steering wires 114 to provide tension thereto. In some embodiments, the springs may be disposed within the handle and attached to a proximal end of the plurality of steering wires 114. Other configurations are also contemplated.

In some embodiments, since the plurality of steering wire sheaths 116 and the plurality of steering wires 114 may be passed through and/or interwoven with the reinforcing braid 108, the overall profile of the guide catheter 100 may not be significantly increased and/or may be reduced. The plurality of steering wire sheaths 116 and the reinforcing braid 108 may be supported and bound together by an outer layer 110 that may be formed primarily of a biocompatible polymer or other suitable material such as, but not limited to, materials disclosed below.

In some embodiments, the inner layer 106 may be formed using a suitable process or technique such as extrusion, injection molding, and so forth. In some embodiments, the reinforcing braid 108 may be formed by disposing the first plurality of the wires 109 and the second plurality of the wires 109' in a suitable arrangement that may provide flexibility, pushability, torqueability, or the like to the guide catheter 100 and/or the tubular member 102. In some embodiments, the plurality of steering wires 114 may be inserted through the reinforcing braid 108 along with the plurality of steering wire sheaths 116. In some embodiments, the plurality of steering wire sheaths 116 may be passed through or interwoven with the reinforcing braid 108 as the reinforcing braid 108 is formed, and the plurality of steering wires 114 may be inserted into the plurality of steering wire sheaths 116 later. In some embodiments, the outer layer 110 of the guide catheter 100 may be disposed over the reinforcing braid 108 such that the reinforcing braid 108 and/or the plurality of steering wire sheaths 116 (and the plurality of steering wires 114 slidably received therein) may be partially or completely embedded within the outer layer 110. In some such scenarios, the outer layer 110 may be disposed over the reinforcing braid 108 as a molten material. In some embodiments, the molten material (i.e., the outer layer 110) may flow at least partially through the reinforcing braid 108 and into contact with the inner layer 106. Upon cooling, the molten material may solidify to form the outer layer 110.

In some embodiments, the outer layer 110 may be provided with a desired thickness and/or structure by techniques such as co-extrusion, injection molding, or other suitable techniques. In some embodiments, the outer layer 110 may be formed separately and disposed about and coupled to the reinforcing braid 108 and/or the inner layer 106. In some embodiments, coupling may be done by adhesive means including, but not limited to, epoxy resins, acrylic resins, polyurethane adhesives, colloidal epoxy silica, or the like. In some embodiments, the coupling may be mechanical coupling, such that the outer layer 110 may include a groove within which the reinforcing braid 108 may be secured to couple the reinforcing braid 108 with the outer layer 110.

Figure 3:
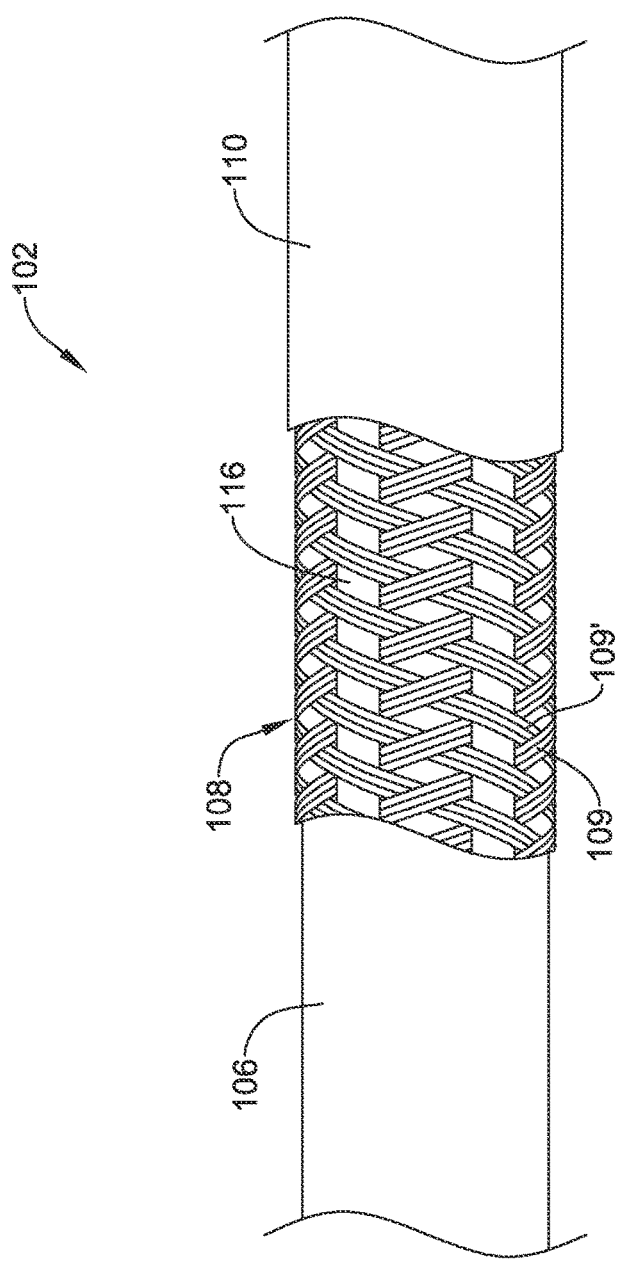
FIG. 3 illustrates a partial cut-away side view of the example guide catheter of FIG. 1.

Referring back to the reinforcing braid 108, in some embodiments, the first plurality of wires 109 and the second plurality of wires 109' may be arranged to form a regular braid having a uniform arrangement. In some embodiments, the first plurality of wires 109 and the second plurality of wires 109' may be arranged to form an irregular braid having a non-uniform arrangement. In some embodiments, the reinforcing braid 108 may include a combination the uniform arrangement and the non-uniform arrangement. In some embodiments, the reinforcing braid 108 may include a first plurality of wires 109 that may include three individual wires arranged side-by-side and a second plurality of wires 109' that may also include three individual wires arranged side-by-side, as seen for example, in FIG. 3. In some embodiments, a first plurality of wires 109 may be arranged helically around the inner layer 106 in a first direction and a second plurality of wires 109' may be arranged helically around the inner layer 106 in a second direction opposite the first direction. In some embodiments, the first plurality of wires 109 and the second plurality of wires 109' may be arranged such that the first plurality of wires 109 alternates between passing over and under the second plurality of wires 109'. In some embodiments, such an arrangement may form a regular braid with a substantially uniform gap between the first plurality of wires 109 and the second plurality of wires 109' defining a plurality of interstices 113. In some embodiments, such an arrangement may form an irregular braid with a non-uniform gap between the first plurality of wires 109 and the second plurality of wires 109' defining a plurality of interstices 113.

In some embodiments, the first plurality of wires 109 and the second plurality of wires 109' may be arranged in a side-by-side fashion to form a 3×3 braid. Other quantities and/or configurations are also contemplated (i.e., 1×2, 1×3, 1×4, 2×2, 2×3, 2×4, 3×4, 3×5, etc.). A total of 32, 48, 64, or other suitable quantity of wires may be used to form the reinforcing braid 108. In some embodiments, the first plurality of wires 109 and/or the second plurality of wires 109' may include one, two, three, four, five, six, or other suitable number of individual wires each. In some embodiments, the first plurality of wires 109 and the second plurality of wires 109' may each include a different number of individual wires. In some embodiments, the plurality of steering wires 114 and the plurality of steering wire sheaths 116 may be passed through the interstices 113 of the reinforcing braid 108. Finally, an outer layer 110 may be disposed over the reinforcing braid 108.

In some embodiments, the reinforcing braid 108 may be formed by weaving a first plurality of wires 109 and a second plurality of wires 109' such that the first plurality of wires 109 alternate between passing over and then under the second plurality of wires 109'. In some embodiments, the reinforcing braid 108 can be a mesh, where the first plurality of wires 109 and the second plurality of wires 109' may be formed with different diameters or dimensions woven together.

In some embodiments, the first plurality of wires 109 and the second plurality of wires 109' may be formed using the same or different materials. In some embodiments, the first plurality of wires 109 may be formed using a first material and the second plurality of wires 109' may be formed using a second material. In some embodiments, the first material and the second material may be the same material, or the first material and the second material may be different materials. In some embodiments, the first material and/or the second material may be a metallic material, a non-metallic material, a ceramic material, a composite material, or a combination thereof. In some embodiments, the first plurality of wires 109 and the second plurality of wires 109' may be formed of a first metallic material. In some embodiments, the first plurality of wires 109 may be formed using a first metallic material and the second plurality of wires 109' may be formed using a second non-metallic material different from the first metallic material. Other materials, arrangements, and/or configurations are also contemplated. Examples of some materials for the first plurality of the wires 109 and the second plurality of wires 109' may include stainless steel, gold, platinum, titanium, nitinol, Dacron, PTFE, polycarbonate, HDPE, nylon, silk, PEEK, or other suitable materials such, but not limited to, materials disclosed below.

In most embodiments, the plurality of steering wires 114 may be formed using a suitable material that may be substantially flexible as well as has strength for torque control and limited stretch. Some suitable materials may include stainless steel, titanium, platinum, gold, silver, a suitable alloy, and other suitable materials, such as, but not limited to, materials disclosed below. In some embodiments, one or more of the plurality of steering wires 114 may include or be formed from an optical fiber capable of functioning as a sensor wire. In some embodiments, one sensor wire may be disposed alongside, within, and/or attached to one of the plurality of steering wires 114. In some embodiments, a sensor wire may include an integrated FBG (fiber bragg gratings) sensor. In some embodiments, a sensor wire may include one or more FBG sensors disposed along the length of the sensor wire. In some embodiments having a sensor wire and/or one or more FBG sensors, the one or more FBG sensors may provide a feedback mechanism to the operator indicating a degree of bending or rotation of the guide catheter 100 and/or the tubular member 102.

In some embodiments, the plurality of steering wire sheaths 116 may be formed using a suitable polymer such as polyethylene, nylon, PEEK, PTFE, or other suitable polymers, such as, but not limited to, materials disclosed below. In some embodiments, a cross-sectional shape of the plurality of steering wires 114 and/or the plurality of steering wire sheaths 116 may be round, ovoid, triangular, rectangular, square, polygonal, or other suitable cross-sectional shape(s).

Figure 3A:
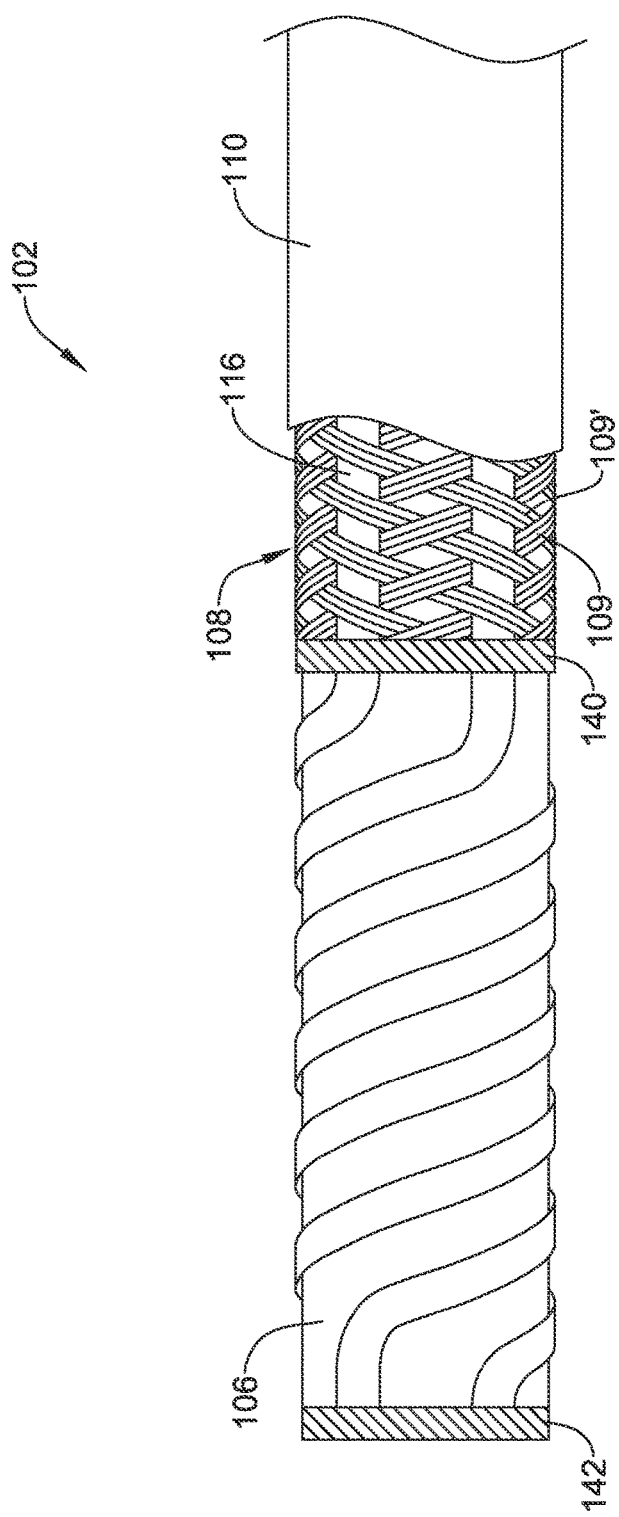
FIG. 3A illustrates a partial cut-away side view of an example guide catheter.

In some embodiments, the guide catheter 100 and/or the tubular member 102 may include a means for rotating at least a portion of the guide catheter 100 and/or the tubular member 102. In some embodiments, as seen in FIG. 3A for example, the guide catheter 100 and/or the tubular member 102 may include a reinforcing braid 108 that terminates at a distal end disposed in a middle portion of the guide catheter 100 and/or the tubular member 102. In some embodiments, a proximal ring 140 may be disposed at the distal end of the reinforcing braid 108. The plurality of steering wires 114 and/or the plurality of steering wire sheaths 116 may extend through the proximal ring 140, such as by passing through corresponding apertures in the proximal ring 140. In some embodiments, one, some or all of the plurality of steering wires 114 and/or the plurality of steering wire sheaths 116 may extend distally in a helical or spiral pattern from the proximal ring 140 to a distal ring 142 disposed at a distal end of the guide catheter 100 and/or the tubular member 102. The proximal ring 140, the distal ring 142, the plurality of steering wires 114, and/or the plurality steering wire sheaths 116 may be disposed about the inner layer 106 and/or embedded in the outer layer 110. In some embodiments, the proximal ring 140 and/or the distal ring 142 may be at least partially embedded in the inner layer 106, and in such embodiments, the portion of the proximal ring 140 not embedded in the inner layer 106 may be covered by or embedded in the outer layer 110.

In some embodiments, the proximal ring 140 and/or the distal ring 142 may be formed from a metallic material, such as, but not limited to, the metallic materials listed below. In some embodiments, the proximal ring 140 and/or the distal ring 142 may be formed from a stiff polymeric material, such as, but not limited to, the polymeric materials listed below. In some embodiments, the proximal ring 140 and/or the distal ring 142 may be formed from a composite material and/or combinations of metallic and polymeric materials. Other suitable materials may also be used.

In some embodiments, a distal end of the plurality of steering wires 114 and/or the plurality of steering wire sheaths 116 may be fixedly attached to the distal ring 142. In some embodiments, the plurality of steering wires 114 and/or the plurality of steering wire sheaths 116 may extend distally of the distal ring 142, and may include a distal stopping feature to prevent pulling the plurality of steering wires 114 proximally through the distal ring 142. In some embodiments, simultaneous actuation of all of the plurality of steering wires 114 may cause a distal portion (i.e., a portion distal of the proximal ring 140) of the guide catheter 100 and/or the tubular member 102 to rotate. In some embodiments, the plurality of steering wires 114 and the plurality of steering wire sheaths 116 may include one or more steering wires 114 that may be substantially straight and/or longitudinally-oriented between the proximal ring 140 and the distal ring 142, and one or more steering wires 114 may be helically or spirally oriented between the proximal ring 140 and the distal ring 142. In these embodiments, the longitudinally-oriented wires may effect bending movement to the distal end of the guide catheter 100 and/or the tubular member 102 upon actuation, and the helically-oriented wires may effect rotation of a distal portion of the guide catheter 100 and/or the tubular member 102 upon actuation.

Figure 4:
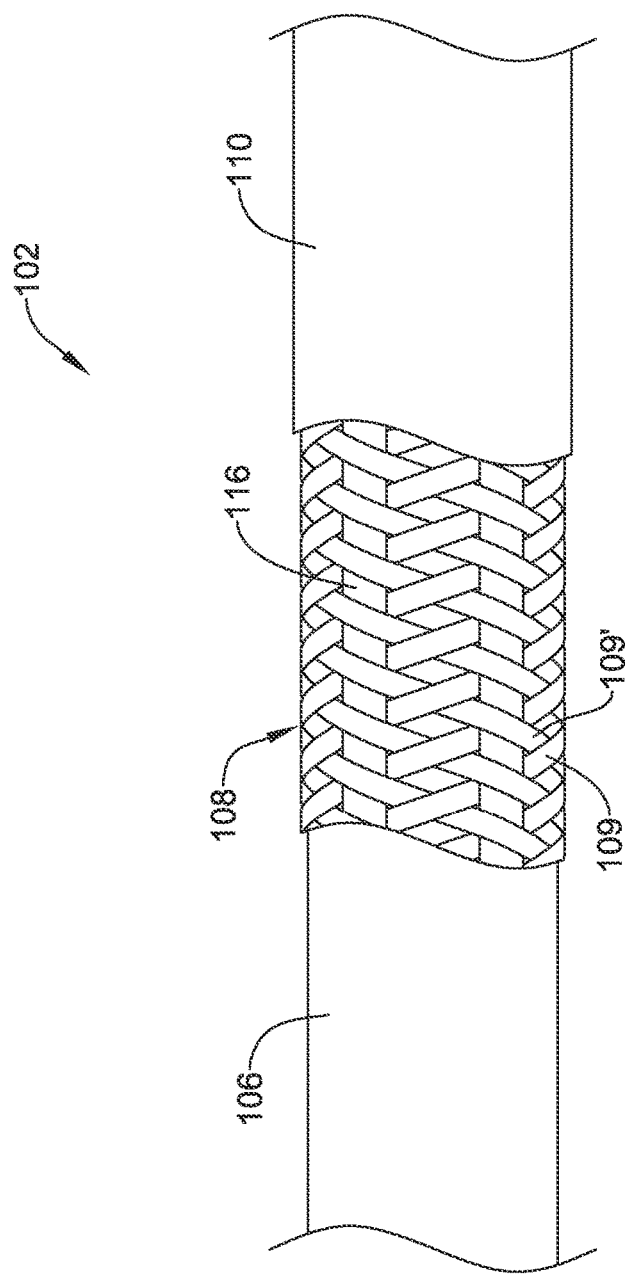
FIG. 4 illustrates a partial cut-away side view of the example guide catheter of FIG. 1.

In some embodiments, the first plurality of wires 109 and the second plurality of wires 109' may be flat ribbon wires braided together in a regular arrangement, as seen for example in FIG. 4, or in an irregular arrangement (not shown). The flat ribbon wires may be arranged such that adjacent turns of the flat ribbon wires may be spaced apart from each other. The plurality of steering wires 114 and the plurality of steering wire sheaths 116 may be passed through and/or interwoven with the reinforcing braid 108 through the interstices 113 between the flat ribbon wires, in a manner similar to that described above.

Figure 5:
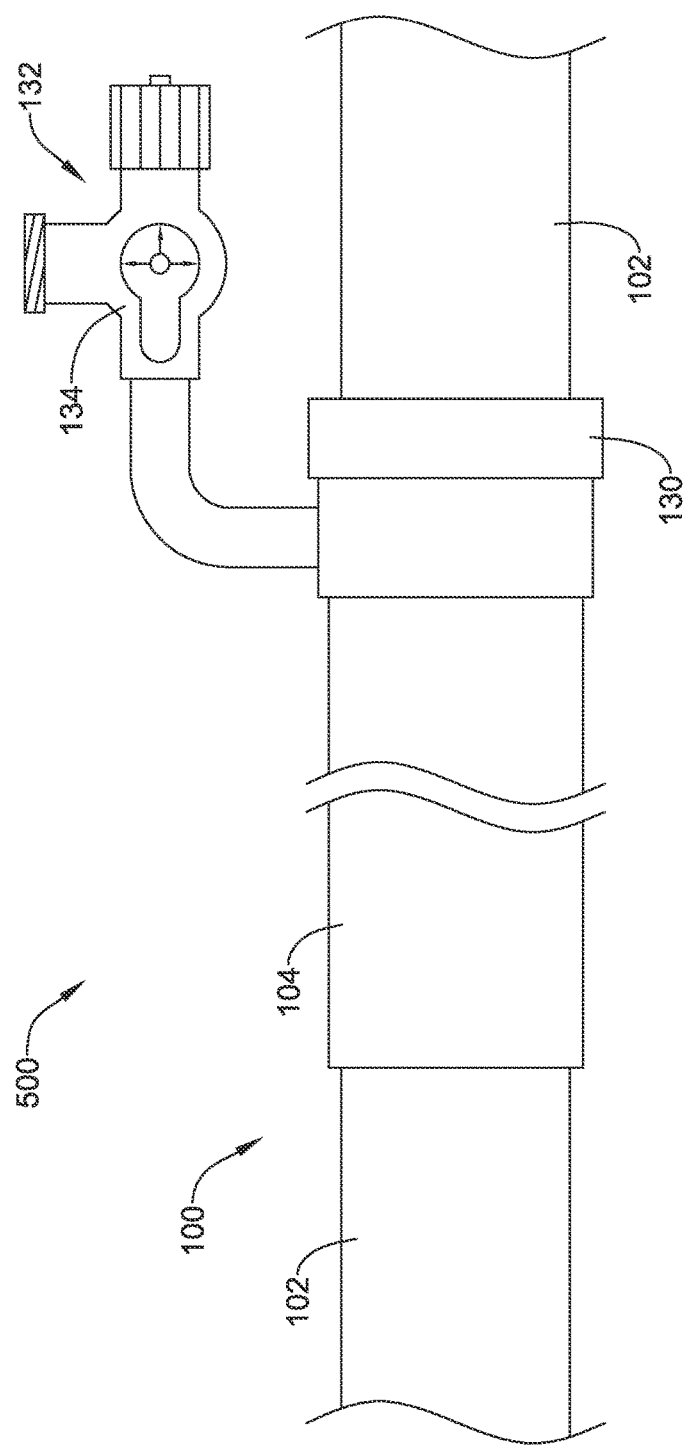
FIG. 5 illustrates perspective view of a portion of an example catheter system.

FIG. 5 illustrates a catheter system 500 that may include a guide catheter 100 and an introducer sleeve 104 disposed about the guide catheter 100 such that the guide catheter 100 may support the introducer sleeve 104. In some embodiments, the guide catheter 100 may pass completely through the introducer sleeve 104. In some embodiments, the introducer sleeve 104 may include a backflow seal 130 coupled to the introducer sleeve 104 at a proximal end. In some embodiments, the backflow seal 130 may include a sealing element at a proximal end thereof, the sealing element being configured to rest against an outer surface of the guide catheter 100 and/or the tubular member 102. In some embodiments, the sealing element may be disposed within the backflow seal 130 and/or along or extending inwardly from an inner surface of the backflow seal 130. In some embodiments, the backflow seal 130 and/or the sealing element may prevent fluid backflow between the guide catheter 100 and/or the tubular member 102, and the introducer sleeve 104 in a proximal direction past the backflow seal 130 and/or the sealing element. In some embodiments, the backflow seal 130 and/or the sealing element may serve as a bearing surface permitting the guide catheter 100 and/or the tubular member 102 to slide and/or translate axially through the introducer sleeve 104. In some embodiments, once the introducer sleeve 104 has been located within an entry point hole or opening, the guide catheter 100 and/or the tubular member 102 may slide axially within the introducer sleeve 104 to facilitate positioning a distal end or a distal tip of the guide catheter 100 and/or the tubular member 102 at a target location.

In some embodiments, the catheter system 500 may further include a flush port element 132 operably connected to a proximal portion of the introducer sleeve 104 and/or the backflow seal 130. The flush port element 132 may include a stopcock 134 fluidly connected to a proximal portion of the introducer sleeve 104 distal of the backflow seal 130 and/or the sealing element such that the stopcock 134 may enable flushing a fluid distally from the backflow seal 130 and/or the sealing element between an inner surface of the introducer sleeve 104 and an outer surface of the guide catheter 100 and/or an outer surface of the tubular member 102. In some embodiments, flushing a fluid between the introducer sleeve 104 and the guide catheter 100 and/or the tubular member 102 may deliver the fluid distally into the blood stream and may remove an obstruction. In some embodiments, the fluid may be a blood thinner, contrast agent, antibiotic drug, therapeutic agent, saline solution, or other biocompatible fluid. In some embodiments, the flush port 132 and/or the stopcock 134 may also allow taking or drawing a blood sample from the backflow seal 130 and/or the introducer sleeve 104 for diagnostic purposes. In other words, the backflow seal 130 and/or the sealing element may prevent fluid from flowing proximally through or past the backflow seal 130 and/or the sealing element while permitting fluid to be flushed distally from the backflow seal 130 and/or the sealing element.

Various embodiments disclosed herein are generally described in the context of medical catheterization through the radial artery. It is understood, however, that embodiments of the disclosure have applicability in other contexts, such as delivering therapeutic devise or agents within other vessels of the body, including other arteries, veins, and vasculature (e.g., cardiac and urinary vasculature and vessels), and other tissues of the body, including various organs.

The materials that can be used for the various components of the guide catheter 100, the tubular member 102, the introducer sleeve 104, the inner layer 106, the outer layer 110, the wires 109, 109', 114, and/or sheaths 116, etc. (and/or other devices disclosed herein) may include those commonly associated with medical devices. For simplicity purposes, the following discussion makes reference to the guide catheter 100, the tubular member 102, and/or the introducer sleeve 104. However, this is not intended to limit the devices and methods described herein, as the discussion may be applied to other similar tubular members and/or expandable members and/or components of tubular members and/or expandable members disclosed herein.

The guide catheter 100, the tubular member 102, and/or the introducer sleeve 104 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the guide catheter 100, the tubular member 102, and/or the introducer sleeve 104 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guide catheter 100, the tubular member 102, and/or the introducer sleeve 104 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guide catheter 100, the tubular member 102, and/or the introducer sleeve 104 to achieve the same result.

In some embodiments, a degree of Magnetic Resonance Imaging (MRI) compatibility may be imparted into the guide catheter 100, the tubular member 102, and/or the introducer sleeve 104. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the guide catheter 100, the tubular member 102, and/or the introducer sleeve 104 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A guide catheter, comprising:
   an inner layer defining a lumen extending therethrough;
   a reinforcing braid disposed about the inner layer, the reinforcing braid comprising a plurality of wires interwoven with each other in an alternating over and under fashion;
   a plurality of steering wires interwoven through the reinforcing braid; and
   an outer layer disposed about the reinforcing braid;
   wherein at least a portion of the reinforcing braid is embedded within the outer layer.

2. The guide catheter of claim 1, wherein the plurality of steering wires each include an elongate wire slidably disposed within a lumen of a polymer sheath.

3. The guide catheter of claim 1, wherein the reinforcing braid includes a first plurality of wires disposed helically about the inner layer, and a second plurality of wires disposed helically about the inner layer in an opposite direction from the first plurality of wires and interwoven with the first plurality of wires.

4. The guide catheter of claim 3, wherein the plurality of steering wires is disposed between the first plurality of wires and the second plurality of wires.

5. The guide catheter of claim 3, wherein the first plurality of wires comprises a first metallic material.

6. The guide catheter of claim 5, wherein the second plurality of wires comprises the first metallic material.

7. The guide catheter of claim 5, wherein the second plurality of wires comprises a second metallic material different from the first metallic material.

8. The guide catheter of claim 5, wherein the second plurality of wires comprises a non-metallic material.

9. The guide catheter of claim 3, wherein the first plurality of wires comprises a first non-metallic material.

10. The guide catheter of claim 9, wherein the second plurality of wires comprises the first non-metallic material.

11. The guide catheter of claim 9, wherein the second plurality of wires comprises a second non-metallic material different from the first non-metallic material.

12. The guide catheter of claim 9, wherein the second plurality of wires comprises a metallic material.

13. The guide catheter of claim 3, wherein the first plurality of wires comprises flat ribbon wire, wherein adjacent turns of the flat ribbon wire are spaced apart from each other.

14. The guide catheter of claim 3, wherein the second plurality of wires comprises flat ribbon wire, wherein adjacent turns of the flat ribbon wire are spaced apart from each other.

15. A catheter system, comprising:
   a guide catheter comprising:
      an inner layer defining a lumen extending therethrough;
      a reinforcing braid disposed about the inner layer, the reinforcing braid comprising a plurality of wires interwoven with each other in an alternating over and under fashion;
      a plurality of steering wires interwoven through the reinforcing braid;
      an outer layer at least partially disposed about the reinforcing braid; and
      an introducer sleeve slidably disposed about and supported by the guide catheter; and
   a flush port element operably connected to the introducer sleeve.

16. The catheter system of claim 15, wherein the introducer sleeve includes a backflow seal at a proximal end thereof, the backflow seal cooperating with a outer surface of the guide catheter to prevent fluid flow therethrough.

17. The catheter system of claim 15, wherein the flush port element includes a stopcock fluidly connected to a proximal portion of the introducer sleeve for flushing between the introducer sleeve and the guide catheter.

18. The catheter system of claim 15, wherein the guide catheter passes completely through the introducer sleeve.

19. The catheter system of claim 15, wherein the reinforcing braid is mechanically interlocked with the outer layer.

20. The catheter system of claim 19, wherein at least a portion of the reinforcing braid is embedded within the outer layer.

\* \* \* \* \*